United States Patent [19]

Burney

[11] Patent Number: 4,606,233

[45] Date of Patent: Aug. 19, 1986

[54] BAG SAMPLER

[75] Inventor: Curtis M. Burney, Fort Lauderdale, Fla.

[73] Assignee: Nova University, Ft. Lauderdale, Fla.

[21] Appl. No.: 636,092

[22] Filed: Jul. 30, 1984

[51] Int. Cl.[4] .......................... G01N 1/12; G01N 1/14
[52] U.S. Cl. ............................... 73/864.63; 73/864.34; 294/68.1
[58] Field of Search .......... 73/864.63, 864.66, 864.67, 73/170 A, 864.34; 294/68.1, 68.25, 68.26, 68.21, 68.22

[56] References Cited

U.S. PATENT DOCUMENTS

| | | | |
|---|---|---|---|
| 1,097,876 | 5/1914 | Pruyn | 294/68.1 X |
| 2,464,834 | 3/1949 | Taylor | 73/170 A |
| 3,242,740 | 3/1966 | Niskin | 73/864.67 X |
| 3,367,190 | 2/1968 | Bieri | 73/864.67 |
| 3,412,498 | 11/1968 | Niskin | 73/170 A X |
| 4,462,265 | 7/1984 | Rein | 73/864.34 X |

FOREIGN PATENT DOCUMENTS

| | | | |
|---|---|---|---|
| 2101234 | 8/1972 | Fed. Rep. of Germany | 73/864.34 |
| 292097 | 1/1971 | U.S.S.R. | 73/864.63 |
| 390402 | 7/1973 | U.S.S.R. | 73/864.63 |
| 763724 | 9/1980 | U.S.S.R. | 73/864.67 |
| 800783 | 2/1981 | U.S.S.R. | 73/864.63 |

OTHER PUBLICATIONS

"A Hermetically Sealed Combination Sampler and Degasser"; *Oceanology (USA);* vol. 16; Sep. 1976; pp. 94-95; V. I. Avilov.

Primary Examiner—Stewart J. Levy
Assistant Examiner—Tom Noland
Attorney, Agent, or Firm—Eugene F. Malin

[57] ABSTRACT

A simple nonmetallic device allowing the gentle enclosure of a few hundred liters of water from discrete depths in flexible plastic bags for in situ time series studies. The disposable bags close without rigid moving parts, remain in situ and are pump sampled from the surface. The system is suitable for deployment at sea and for radio-tracer experiments.

11 Claims, 4 Drawing Figures

BAG SAMPLER

BACKGROUND OF THE INVENTION

Estimation of the rate of physiological processes of planktonic microorganisms in natural waters is plagued by a question common to all areas of experimental science. Does the act of observing change that which is observed? Enclosure and incubation of natural communities in bottles can, at least in some instances, cause profound changes in community structure. It has been found that phytoplankton species abundances declined by an average of about 20% during 12 to 24 hour incubations in 250 ml bottles. Some protozooplankton groups dissappeared completely and chrophyll and ATP declined 10 to 30%. Other researchers have reported abnormally high rates of photochemical pigment destruction during incubation, which varied inversely with bottle volume. If bottle confinement or sample handling is responsible for such die offs in 12 to 24 hour periods, there must be an even more profound and rapid degradation of the physiological condition of the population.

As an alternative to bottle incubation methods, information on total system metabolism can be obtained from determinatins of plankton biomass and chemical parameters, such as organic and inorganic nutrients, dissolved $O_2$ and total $CO_2$, on samples taken directly from the natural environment at intervals over diel periods. This approach avoids the uncertainties of bottle incubation; however, in open water studies, advective and mixing processes cloud the interpretation of the results irregardless of what precautions are applied. In addition, free water studies usually preclude the use of radiotracers for physiological rate measurements.

SUMMARY OF THE INVENTION

Accordingly, it is an object of this invention to provide a system useful for repeatedly sampling water from preselected depths over periods of up to 48 hours in duration.

It is a further object of this invention to provide a system useful for sampling and estimating process rates of micro-organisms, especially Plankton, in ocean or other natural bodies of water that minimizes disturbance of these micro-organisms.

It is a further object of this invention to provide such a system capable of enclosing such a sample of water in situ, without isolating the sample from surrounding turbulence.

It is a further object of this invention to provide such a system that has no rigid moving parts, and is hence both simple and reliable to operate.

In accordance with these and other objects that shall become apparent hereinafter, the instant invention provides a simple, ship deployable device designed for the Plankton Rate Processes in Oligotrophic Oceans (PRPOOS) program. It allows in situ time series sampling and radio-tracer incubation studies on homogenous water masses of a few hundred liters which had been gently enclosed at depth in self filling flexible plastic bags. The system is also suitable for light-dark experiments and can be fitted with screens for in situ size fraction exclusion studies.

PREFERRED EMBODIMENT OF THE INVENTION

Figure 1:
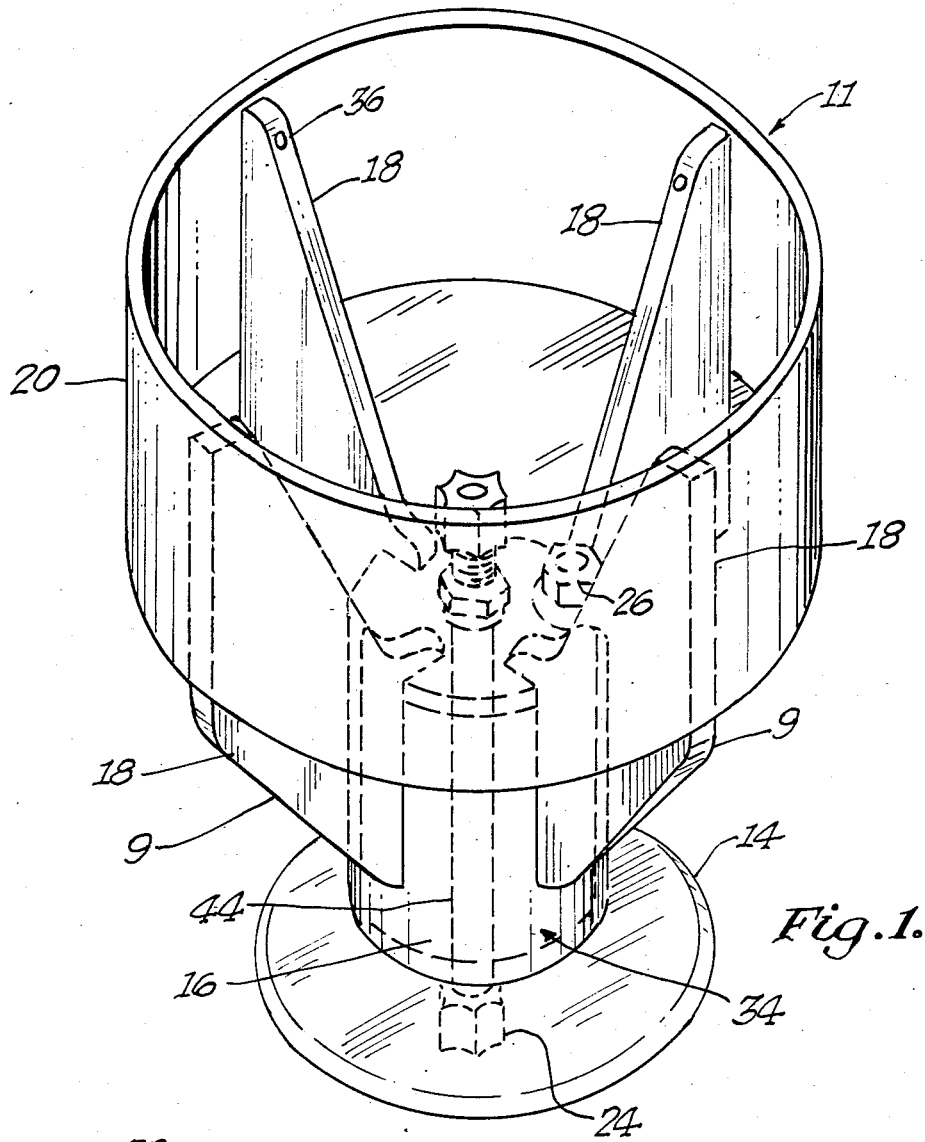
FIG. 1 is an elevational view of the sampler's frame, with the frame's members shown as transparent to better illustrate the frame's structure.
Figure 3:
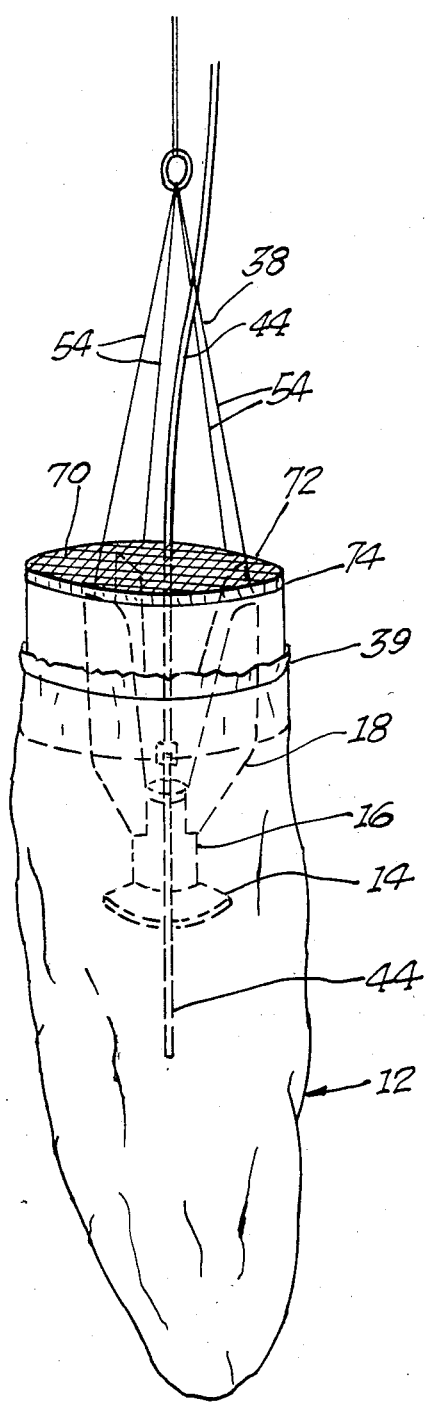
FIG. 3 is an elevational view of the sampling system illustrating an alternative embodiment of the invention.
Figure 2:
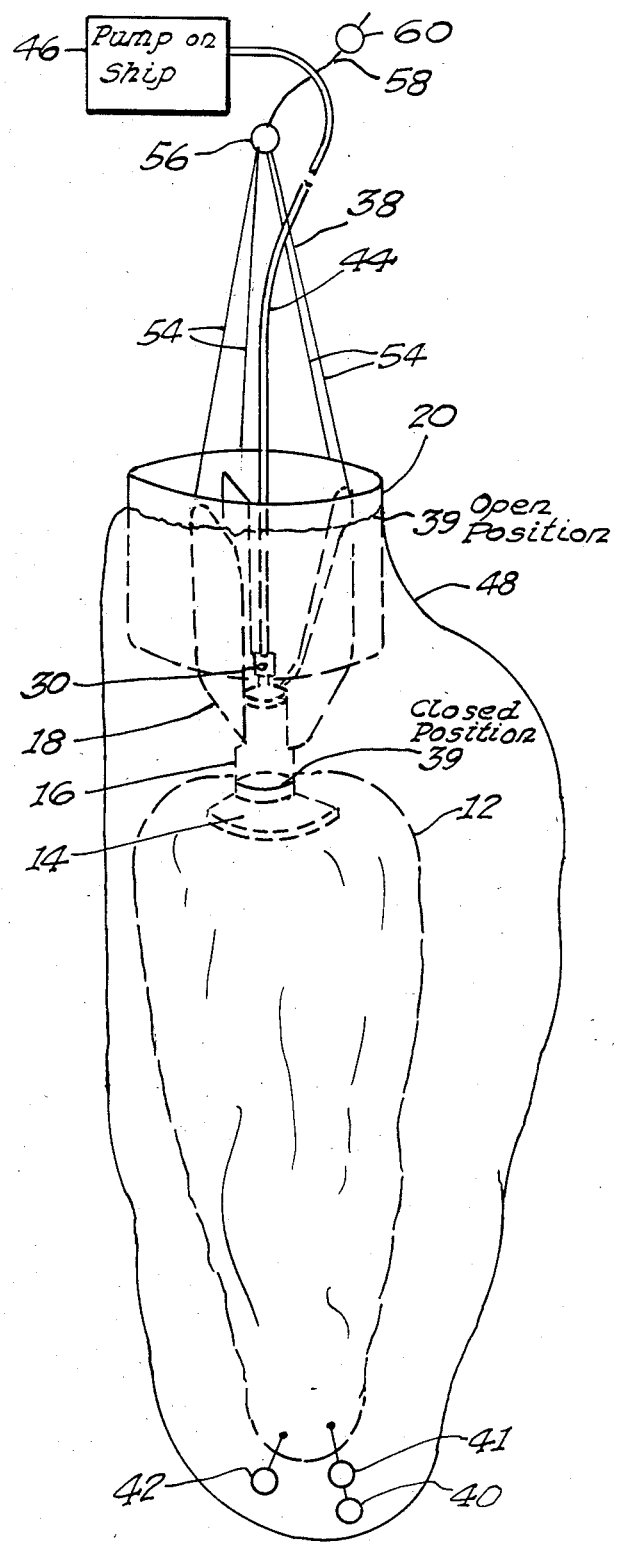
FIG. 2 is an elevational view of the sampling system illustrating its operation.

With particular reference to the drawings, the system shown generally as numeral 10 consists of a rigid plastic frame 11 and a flexible polyethylene bag 12. The frame 11 holds the bag 12 open during filling and allows it to close without employing rigid moving parts. The essential components of the frame (FIG. 1) consist of a bag retaining flange 14 bonded to a cylindrical central core 16 attached to four heavy struts 18 which support a large hoop frame 20 at the front end. The central core 16 is a sealed hollow chamber 34, which is penetrated by an internal sampling tube 44 with polypropylene compression tube fittings 24 at both ends. The sampling tube 44 passes through the central core 16, extends a few centimeters behind the retaining flange 14, and is held in place by both the front and rear compression fittings 24. A plugged port 26 in the forward end of the central core 16 allows this chamber 34 to be ballasted with water to achieve neutral buoyancy, if desired. A plurality of holes 36 through the extreme forward ends of the struts 18 provide attachment points for a towing harness 38 (FIGS. 2 and 3).

Hoop frames 20 have been constructed of polyvinyl chloride (PVC), acrylic (Plexiglas) and polycarbonate (Lexan) plastics. The former provides the best mix of workability, strength and price. Polycarbonate provides superior strength, impact resistance and transparency but its intractability to fabrication (especially heat forming of hoops from sheet stock) significantly increases costs. All joints are cemented and secured with screws for greatest strength. Nylon screws are used for applications where trace metal contamination must be avoided.

Dimensions are dictated by the application. For shallow water work and deployment from small boats, frames 20 with a 30 cm hoop diameter are useful, while frames 20 with 46 cm diameter hoops are more appropriate for larger volume work, yet are small enough to be hand deployed. The diameter of the central core 16 is one third that of the hoop 20. No other dimensions are critical as long as the general form in FIG. 1 is followed. The outward edges 9 of the struts 18 and the edge of the retaining flange 14 are rounded and perfectly smooth.

Polyethylene bag 12 with a mouth diameter from about 1.3 to 2 times that of the frame hoop has produced best results. Bags 61 cm in diameter, 160 to 230 cm long and 76 um (3 mil) to 127 um (5 mil) thick have been used most frequently. For use, one or more surgical tubing rings must be installed in the mouth of each bag 12 as follows:

The free edge of the material at the mouth of the bag 12 is folded back 5 or 6 cm around the circumference and heat sealed to the body of the bag 12 such that an enclosed channel around the mouth is produced. This is easily done with a small, open jawed, hand held impulse sealer, such as a Packaging Aids Corp. (San Francisco, Ca.) Future model. A 2 to 3 cm diameter hole is then cut in the outside of the channel and one end of a length of stiff, bendable, polyethylene tubing slightly longer than that of bag 12's circumference is inserted into the channel and threaded all the way around the mouth and back out the hole. This is used as a leader for insertion of the elastic ring. One end of a length of amber latex surgical grade tubing of about 8 mm inside diameter with a 1.6 mm wall thickness (5/16×1/16 inch) is pushed 2 or 3 cm over the end of the polyethylene tube and the other end of the leader is withdrawn from the bag 12 while working the surgical tubing into the channel until it is threaded around the mouth. Both ends of the surgical tubing are then withdrawn from the channel while bunching up the mouth of the bag 12 until a length of tubing sufficient to form a ring 39 of, optimally, 0.75 the diameter of the frame central core 16 remains inside. The ends of the surgical tubing are then tied with a square knot and the excess tubing trimmed about 1.5 cm from the knot. The knot is then worked through the hole into the channel to prevent it from snagging. To avoid contamination, polyethylene gloves are worn during installation of the elastic band. If two bands in the mouth of the bag 12 are desired to increase holding power of the bag 12 on the frame, a second length of tubing can be threaded through the channel before the first one is withdrawn. Both tubes are then withdrawn simultaneously to produce the proper size elastic bands.

Since polyethylene is buoyant, it is necessary to weight the back end of the bag 12. This can be done by carefully making a second seal across the bag 12, parallel to, and about 5 to 6 cm from, the bottom seal. Grommets (not shown) for weight attachment may be installed between the two seals. During deployment, a weight of 1 to 2 kg should be attached to the bottom of the bag 12 in order to hold the bag 12 vertically in the water so that trapped air may escape out its mouth before closing. This heavy weight 40 should be attached via a dissolving salt link 41 so that it will be dropped a preselected time after deployment. Small animal salt licks of about 5 cm diameter (available in pet shops) are suitable dissolving links. A second weight 42 of about 0.5 kg should be directly attached to the bottom of the bag 12 to keep it from floating up during the experiment.

FIG. 2 shows the basic system 10 deployed for filling and closed for sampling. The bag 12 is loaded on the frame hoop 20 by stretching the surgical tubing ring 39 over the retaining flange 16 and then over the rear edge of the hoop 20. The latter operation requires two or three people and some effort, especially if a double band is installed. When initially lowered into the water, the device 10 will float. The frame hoop 20 must be pushed beneath the surface by hand or with a boat hook. When submerged in the vertical position (before the heavy weight has released), gentle tugging on the suspension line will facilitate the escape of any air trapped during deployment. The sampler 10 is then lowered to the desired depth. After the heavy weight 40 has separated, a long steady pull on the suspension line by hand, will fill the bag 12. The drag of the filled bag 12 slips its mouth off the frame hoop 20, down along edges 9 until the elastic ring 39 snaps securely around the central core 16, trapping the contained water mass. Water is then pumped from the bag 12 to the surface through the sampling tube 44 with a peristaltic pump 46. Because the volume of water removed from bag 12 is small compared with bag volume, even over extended sampling times, biological communities within bag 12 is not disturbed appreciably. For studies requiring small volumes per sample on the order of (a few liters), a hand cranked peristaltic pump such as the Tat Engineering Co. (North Branford, Conn.) model 650 is adequate and reliable. Larger volume requirements require an electric powered peristaltic pump. The sampling tube may be of any material which will not collapse under partial vacuum and will not contaminate the analyses.

If desired, the bag 12 may be lowered to depth in a closed configuration. After loading on the frame 20 in the open position, the belly of the bag 12 is secured around the central core 16 from the outside by wrapping with a heavy rubber band (not shown). During this operation, the bag 12 is rolled tightly to exclude as much air as possible. The rubber band is held in place with a salt dissolving link which must be timed to release a few minutes prior to release of the heavy weight from the back end of the bag 12 so that the bag will open while still held in the vertical position, allowing trapped air to escape.

For use under conditions where wave action and ship motion put considerable strain on the system which can slip the mouth of the bag over the retaining flange, enclosure of the entire system in an external support net (not shown) is recommended. After loading a bag 12 on the frame 20, a 3 to 4 cm mesh nylon net of the same general shape as the bag is drawn up around the bag and secured at the forward edge of the frame by weaving a heavy length of nylon line in and out of the mesh around the net mouth and also passing this line through the loops of the four bowlines used to attach the towing harness to the frame. It is important that the length of the support net is sufficient to allow the bag 12 to close and that it is not too long to support the enclosed water mass and transfer the point of stress from the mouth of the bag 12 to the towing harness 38. The length of the net should be exactly equal to the distance from the forward edge of the frame hoop to the rear of the bag in the closed configuration. Heavy deployment weight 42 should be suspended outside the net via a line passing through the mesh to the rear of the bag (not shown).

Figure 4:
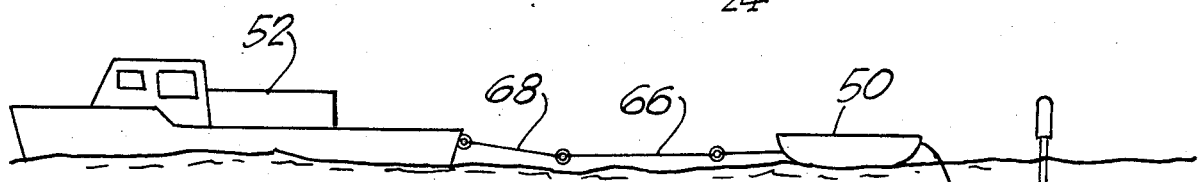
FIG. 4 is a plan view illustrating deployment of the invention.
Figure 4:
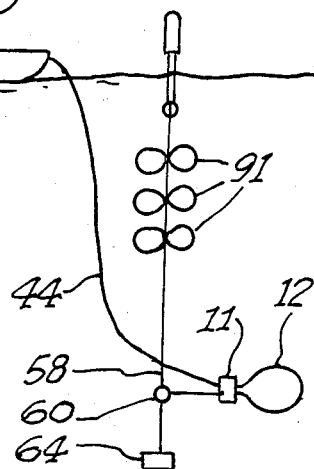

FIG. 4 illustrates the invention deployed at sea. Line 58 is illustrated as buoyed by spar buoy and subsurface floatation balls 91, which prevent jerking of the sampler by wave action in rough seas. In calm inshore waters buoy 90 and balls 91 may be dispensed with.

When used at sea, it is advantageous to launch and suspend the bags from an inflatable boat 50 tethered to the mother ship 52 to prevent lines and sampling tubes from fouling the screws of ships 52, and to protect the bag 12 from violent jerking caused by ship roll and surge. Four equal lengths of vinyl coated 0.635 cm (¼ inch) diameter Kevlar line 54 are tied through the holes 36 in the forward ends of the frame struts 18 and the opposite ends secured to a double epoxy dipped steel towing ring 56 to form harness 38. All knots should be bowlines with their loops seized with a nylon cable tie applied just above each knot. The Kevlar suspension line 58 attached to this ring 56 should include a second epoxy coated ring 60 about 2 m above the towing harness 38. After filling and closing the bag 12 at the desired depth, the sampler is pulled up to within 2 m of the boat and another line 62, about 5 m long is tied to the second ring 60. A weight 64, (half a standard concrete block is sufficient) is attached to the opposite end of this line 62 and the bag 12 is lowered back to the desired depth where it assumes a horizontal position relative to the vertical weight line 62 due to a current or ship drift (as shown in FIG. 4). In actual practice, two separate rigs have been simultaneously deployed at sea from the same boat in this manner without tangling. For use in high sea states, the use of subsurface floatation and a spar buoy between the rubber boat and the bag protects the bag from violent jerking (FIG. 4a).

Shock absorber lines 66 should be used in the tether line 68 between ship 52 and rubber boat 50 as well as in the bag suspension line 61 between the two metal rings 56 and 60. Simple shock links can be made by tying a loop made from an approximately 800 cm length of heavy wall, high quality surgical tubing through two dropper loops in the line tied 1 m apart.

The peristaltic pump 46 used for sampling may be located on the ship 52, but for sampling of dissolved oxygen, better results are obtained by mounting the pump in the boat 50 such that water was pushed, (rather than sucked under vacuum) from sea level to the ship. The pump 46 was properly covered and powered by an extension cord from the ship 52. All electrical connections should be securely taped prior to deployment. The system worked well, even in rough seas, and allows for high precision replicate oxygen determinations.

The volume of water captured in the bag 12 depends on the bag size, the tension of the stretched elastic ring 39 on the hoop frame 20, the physical positioning of the bag mouth on the hoop frame 20 during loading, the diameter of the frame 20 and the smoothness of the pull during the filling/closing maneuver. The captured volume can be determined by pumping a known concentration of any measurable dissolved material down the sampling tube 44 into the filled bag followed by several tube volumes of water. After mixing, the concentration of this material in the bag 12 is determined and the volume of water which diluted the original quantity of material can be calculated. This was done using saturated solutions of fluorescein dye in sea water. One liter of concentrated solution was pumped down the sampling tube after the bag had been filled and closed. The bag 12 was mixed by gentle pulling on the suspension lines for about 30 seconds. Samples were taken at 5 to 10 minutes after dye addition and again after at least 1 hour. The transmittance of the dye was measured spectrophotometrically at 490 nm and the results compared to a known dilution curve prepared from the same concentrated dye solution. Increasing the tension of the elastic band or loading the bag farther forward on the frame hoop delays closing and increases the captured volume. A 61 cm diameter, 160 cm long bag loaded 2 cm from the rear edge of a 30 cm hoop 20 diameter frame captured 107 liters in a dockside test. The same bag mounted 8 cm from the rear edge of the hoop captured 163 liters. Increasing frame 20 diameter allows for a larger gulp of water and increases captured volume. When mounted 2 cm from the edge of a 46 cm diameter hoop this bag enclosed 222 liters. Jerking on the suspension line while filling can cause the bag to close prematurely. The same bag mounted on the small frame caught only 58 liters in one test when jerked closed. In all tests, there was never any difference in dye concentration between samples taken initially and over 1 hr after dye addition. When deployed offshore the bags constantly change shape in response to water movements and wave action, producing excellent mixing.

Bag diameter is limited to about twice that of the frame hoop because of excessive bunching of the polyethylene at the mouths of larger bag which restricts closing, but bag length is not limited. Bags of 61 cm diameter, 230 cm long and 127 um (5 mil) thickness work well on the 46 cm hoop frames and capture proportionally more water.

The system can be modified for experimental work. In addition to the use of transparent and opaque bags for in-sitn light-dark experiments, Nitex screens 70 down to 20 um pore size can be fitted in the mouths 72 of the frames to exclude desired size fractions from the bag 12. This can be done by unscrewing the tube fitting from the forward end of the central core and inserting the threaded portion of the fitting through a polyethylene washer and then through a hole made in the center of a circle of Nitex mesh. The fitting is then replaced in the central core and the free edges of the Nitex is drawn up over the forward edge of the hoop and secured around the outside with a surgical tubing band 74 mounted far enough forward so as not to interfere with bag loading. Holes through the Nitex must be made to attach the towing harness. Those on the inside may be sealed with silicone cement if desired but those on the outer side are best left open to allow air trapped under the Nitex to escape.

This sampler should not be confused with the numerous experimental ecosystem enclosures employed over the last quarter century. The design is not intended for long term studies but rather to trap a water mass at depth, as simply and gently as possible, without isolating the enclosed organisms from natural turbulence. Although any such system must disturb the natural environment to some degree, this device is much simpler and less disruptive than designs requiring pump filling and/or mechanical mixing, and must expose the enclosed populations to less disturbance and more natural conditions than they experience in bottles.

The instant invention has been shown and described herein in what is considered to be the most practical and preferred embodiment. The numerous parameters and parametric relationships set forth are considered exemplery rather than exclusive. More generally, it is recognized that departures may be made from the preferred embodiment within the scope of the invention, and that obvious modifications will occur to a person skilled in the art.

What I claim is:

1. A system adapted for sampling water, said system comprising:
    a flexible container means for enclosing a sample of said water, said container means having a mouth;
    means for operating said mouth, said means for operating comprising means for holding said mouth open, and means for hermetically sealing said mouth, said means for operating comprising a frame and an elastic ring means for clamping said mouth against said frame; and wherein:
    said elastic ring is fixed about the perimeter of said mouth;
    said means for holding comprises a rim portion of said frame, and said means for hermetically sealing comprises a chamber portion of said frame;
    wherein said elastic ring means is effective to hold open said mouth if elastically clamping said mouth about said rim, and said elastic ring means is effective to hermetically seal said mouth if elastically clamping about said chamber.

2. The system of claim 1, wherein:
    said frame comprises a plurality of struts and a flange;

said frame is generally annular and said chamber is generally cylindrical;

said plurality of struts are rigidly fixed about the inside circumference of said rim and to the outside circumference of said chamber;

said flange is rigidly fixed to said chamber;

each said rim, plurality of struts, chamber, and flange is disposed with respect to one another so that said mouth becomes hermetically sealed by said elastic ring means being displaced from a position about the outer circumference of said rim to a position about said circumference of said chamber and against said flange.

3. The system of claim 2, wherein said means for operating said mouth of said container comprises tube means for withdrawing a portion of said sample of water.

4. The system of claim 3, wherein said tube means passes through, and is hermetically sealed to, said chamber.

5. The system of claim 4, wherein said flexible container means is a flexible bag.

6. The system of claim 1, wherein said means for operating said mouth of said container comprises tube means for withdrawing a portion of said sample of water.

7. The system of claim 6, wherein said flexible container means is a flexible bag.

8. A system for enclosing a submerged water mass, said system including a flexible plastic container and means for automatically closing said plastic container without the use of rigid moving parts, said means comprising a generally cylindrical filling/closing frame including an outer hoop having a concentrically located central core attached thereto via a multiplicity of struts, the plastic container including a surgical tubing band sealed around its mouth for holding said plastic container mouth around the frame hoop during filling and for binding tightly around the central core when closed thereby trapping water in the container whereby the submerged system during filling may be manually pulled through the water permitting water to flow through the frame hoop into the container, the drag of the filled container initiating closure by slipping the surgical tubing ring in the container's mouth off the frame hoop, said ring binding securely around the frame central core and against the retaining flange.

9. The system of claim 8, wherein said plastic container is a flexible bag.

10. A system for sampling an aqueous medium comprising:
   (a) an enclosure adapted to contain a sample of an aqueous medium,
   (b) said enclosure including means defining an opening for receiving the aqueous medium,
   (c) functionally integral means including a first means being so constructed to initially internally contact the means defining said opening for maintaining said opening in an open position and said functionally integral means further including a second means for permitting decrease of the size of said opening,
   (d) said means defining said opening including constricting means constructed and arranged to engage said second means to hermetically seal said opening, said first means has a horizontal cross-sectional area greater than said second means, said first means having a hollow interior communicating with the interior of said enclosure and with a source of aqueous medium and said means defining said opening and said second means being so constructed to prevent entry of the aqueous medium through said opening into said enclosure when said constricting means is engaged with said second means.

11. An article of manufacture for use in a system for sampling water comprising:
   a central tubular core including a sealed hollow chamber and an internal tube penetrating said core, said hollow chamber being sealed about said internal tube, said internal tube being centrally located within said chamber,
   one end of said core including a flange functionally integral therewith,
   a hoop frame functionally integral with the opposed end of said core and having a diameter of at least about three times the diameter of said core,
   the flange having a diameter greater than said core but of lesser diameter than said frame.

* * * * *